US008846010B2

(12) United States Patent
Vaidya et al.

(10) Patent No.: US 8,846,010 B2
(45) Date of Patent: Sep. 30, 2014

(54) SILICONE COMPOUND AND PHOTOPROTECTIVE PERSONAL CARE COMPOSITIONS COMPRISING THE SAME

(75) Inventors: Ashish Anant Vaidya, Bangalore (IN); Nilmoni Ghosh, West Bengal (IN)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 14/111,645

(22) PCT Filed: Apr. 2, 2012

(86) PCT No.: PCT/EP2012/056144
§ 371 (c)(1),
(2), (4) Date: Dec. 3, 2013

(87) PCT Pub. No.: WO2012/143242
PCT Pub. Date: Oct. 26, 2012

(65) Prior Publication Data

US 2014/0086856 A1 Mar. 27, 2014

(30) Foreign Application Priority Data

Apr. 21, 2011 (IN) ......................... 1282/MUM/2011
Aug. 5, 2011 (EP) ...................................... 1176657

(51) Int. Cl.

| | |
|---|---|
| ***A61K 8/58*** | (2006.01) |
| ***A61Q 17/04*** | (2006.01) |
| ***C09B 69/10*** | (2006.01) |
| ***A61K 8/891*** | (2006.01) |
| ***C08G 77/38*** | (2006.01) |
| ***C08G 77/14*** | (2006.01) |
| *C08G 77/12* | (2006.01) |

(52) U.S. Cl.
CPC ............... *A61K 8/585* (2013.01); *C09B 69/101* (2013.01); *A61Q 17/04* (2013.01); *A61K 8/891* (2013.01); *C08G 77/12* (2013.01); *A61K 2800/57* (2013.01); *C08G 77/38* (2013.01); *C08G 77/14* (2013.01)
USPC ............................................ 424/59; 556/436

(58) Field of Classification Search
None
See application file for complete search history.

(56) References Cited

U.S. PATENT DOCUMENTS 4,381,260 A 4/1983 Chu

FOREIGN PATENT DOCUMENTS

| | | |
|---|---|---|
| EA | EP0396376 | 11/1990 |
| RU | 1712374 | 2/1992 |
| RU | 1712374 A1 | 2/1992 |
| WO | WO9960427 | 11/1999 |
| WO | WO0037048 | 6/2000 |

OTHER PUBLICATIONS

PCT International Search Report in PCT application PCT/EP2012/056144 dated May 15, 2012 with Written Opinion.
European Search Report in EP application EP 11 17 6657 dated Jan. 10, 2012.

*Primary Examiner* — Hasan Ahmed
*Assistant Examiner* — Randeep Singh
(74) *Attorney, Agent, or Firm* — Rimma Mitelman

(57) ABSTRACT

The present invention relates to silicone compounds which have photoprotective properties and personal care compositions comprising the same. The present inventors, in developing a sunscreen that gives protection against both UV radiation and visible radiation, found that when a certain moiety generally occurring in nature i.e. hydroxyanthraquinone having uv-visible absorption activity are attached to crosslinked silicone polymers they provide not only the desired photoprotection but also excellent spreadability on skin.

15 Claims, No Drawings

SILICONE COMPOUND AND PHOTOPROTECTIVE PERSONAL CARE COMPOSITIONS COMPRISING THE SAME

TECHNICAL FIELD

The present invention relates to silicone compounds and personal care compositions comprising the same which have photoprotective properties.

BACKGROUND OF THE INVENTION

Solar radiation includes about 5% ultraviolet (UV) radiation, wavelength of which is between 200 and 400 nm. It is further classified into three regions: from 320 to 400 nm (UV-A), 290 to 320 nm (UV-B) and from 200 to 290 nm (UV-C). A large part of UV-C radiation is absorbed by the ozone layer. Scientific studies have indicated that exposure to UV-A and UV-B radiation for short period causes reddening of the skin and localized irritation, whereas continued and prolonged exposure can lead to sunburn, melanoma and formation of wrinkles. It is also reported that UV radiation causes significant damage to hair. Therefore, it is desirable to protect the skin and other keratinous substrates of the human body from the harmful effects of both, UV-A and UV-B radiation.

Further, more and more in the recent past there is evidence that it is also essential that the body is protected against the damaging effects of visible spectrum of light. Visible part of light ranges from 400 to 800 nm. It is believed that continued exposure to visible light is responsible for damaging effects on skin like erythema, pigmentation, thermal damage and free radical production (Effects of Visible Light on the Skin, Photochemistry and Photobiology, Volume 84, Issue 2, Pages 450-462, 2008). Hence in addition to protection from UV rays it is also necessary to get broader spectrum protection which includes visible light. Sunscreens or sun block agents are generally added to personal care compositions to protect the skin from harmful effects of UV radiation.

Organic sunscreens absorb a large fraction of the incident UV radiation, thereby preventing the radiation from coming in contact with the surface of the skin. They have UV absorbing sites, called chromophores, which are primarily responsible for their activity. Some sunscreens absorb UV-A radiation while some absorb UV-B radiation. The present inventors have been working for several years on providing improved methods and compounds for sunprotection purposes. One such approach has been published in Indian Patent application 2084/MUM/2006A where both UV-A and UV-B moieties are attached to a silicone backbone.

Not many compounds and compositions comprising them have been disclosed for providing protection against visible radiation in addition to UV radiation.

U.S. Pat. No. 4,381,260 (Union Carbide, 1983) discloses polymeric dyes where a group L, a divalent group, connects a chromophoric moiety to a polysiloxane moiety together by covalent bonds which imparts color to the polymer molecule. The polymeric dyes of the present invention can be used to dye natural fibers such as silk, wool, and cotton and to color plastics or used as a food dye as well as in pharmaceutical and cosmetic applications.

The present inventors have been working on the problem of providing a sunscreen that gives broad spectrum protection against both UV and visible radiation. They found to their surprise that when certain moieties generally occurring in nature e.g. hydroxyanthraquinones when attached to a silicone polymer provide not only the desired UV and visible light photoprotection but also excellent spreadability on skin and other human keratinous substrates that is essential for providing enhanced photoprotection. Further, the new polymer thus synthesized is highly amenable for further derivatisation with hydrophilic groups that enable self-emulsification of the polymer in topical products. Further, the compound of the present invention gives enhanced sun protection when incorporated in sunscreen compositions comprising conventional UVA and UVB sunscreens.

It is therefore one of the objects of the present invention is to overcome or ameliorate at least one of the disadvantages of the prior art, or to provide a useful alternative.

Another object of the present invention is to provide a compound that gives relatively better UV and visible light protection and at the same time provides relatively high photostability.

Yet another object of the present invention is to provide compounds that give enhanced photoprotection against both UV and visible radiation while having self-emulsifying property to enable incorporation in personal care compositions without the need for additional emulsifiers.

Yet another object of the present invention is to provide for a personal care sunscreen composition that spreads optimally on the substrate to give the desired broad spectrum photoprotection.

SUMMARY OF THE INVENTION

According to one aspect of the invention there is provided a silicone compound of the general formula:

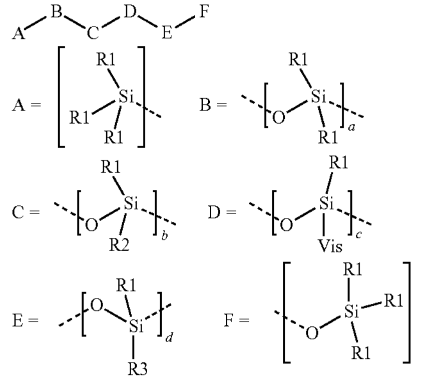

where each R1 is independently a straight or branched alkyl, cycloalkyl, polycycloalkyl, heterocycloalkyl, alkaryl, alkoxy, aryl, aralkyl, alkenyl, alkynyl or fluorocarbon group containing 1-50 carbon atoms;

R2 is R1 or —H, —OH or an organic moiety containing carbon, nitrogen, phosphorous, sulphur, oxygen or silicon atoms;

“Vis” is a UV-visible absorbing moiety selected from the hydroxyanthraquinone group

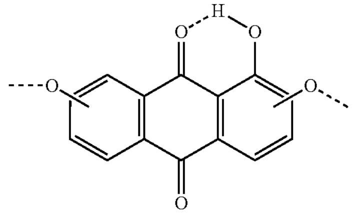

which is capable of covalently linking to a polymer chain;

R3 is R1 or optionally an organic moiety (or spacer) containing carbon, nitrogen, phosphorous, sulphur, oxygen or silicon atoms capable of linking to another polymer;

units A and F are the terminal moieties;

blocks B, C, D and E are non terminal moieties independently positioned between

A and F in any order;

a and c are each independently integers 1-10,000; and b and d each independently an integer 0-10,000.

It is particularly preferred that the units of block E are cross-linked with another series of units of block E through R3 to form a net-like architecture.

According to a preferred aspect of the present invention there is provided a photoprotective personal care composition comprising 0.01 to 10% by weight the silicone compound of the invention.

According to yet another aspect of the present invention there is provided use of the silicone compound of the invention as a sunscreen agent.

According to yet another aspect of the present invention there is provided a process for the preparation of a silicone compound of the invention comprising the steps of reacting:

(i) an Si—H containing siloxane with (ii) a compound of the formula $Vi\text{-}O—(CH_2)_{0\text{-}50}—CH{=}CH_2$ or $CH_2{=}CH—(CH_2)_{0\text{-}50}\text{-}Vi\text{-}O—(CH_2)_{0\text{-}50}—CH{=}CH_2$ or $Vi\text{-}O—(CH_2)_{0\text{-}50}—C{\equiv}CH$ or $CH{\equiv}C—(CH_2)_{0\text{-}50}\text{-}Vi\text{-}O—(CH_2)_{0\text{-}50}—C{\equiv}CH$ where Vi is a uv-visible absorbing moiety selected from the group consisting of hydroxyanthraquinone having alkenyl or alkynyl functionality in the presence of a catalyst and a solvent to obtain the reaction product.

The reaction is preferably carried out in the presence of a difunctional spacer compound having alkenyl or alkynyl groups.

Further preferably the reaction product is added to a swelling agent or synthesized in a swelling agent.

These and other aspects, features and advantages will become apparent to those of ordinary skill in the art from a reading of the following detailed description and the appended claims. For the avoidance of doubt, any feature of one aspect of the present invention may be utilised in any other aspect of the invention. The word "comprising" is intended to mean "including" but not necessarily "consisting of" or "composed of." In other words, the listed steps or options need not be exhaustive. It is noted that the examples given in the description below are intended to clarify the invention and are not intended to limit the invention to those examples per se. Similarly, all percentages are weight/weight percentages unless otherwise indicated. Except in the operating and comparative examples, or where otherwise explicitly indicated, all numbers in this description indicating amounts of material or conditions of reaction, physical properties of materials and/or use are to be understood as modified by the word "about". Numerical ranges expressed in the format "from x to y" are understood to include x and y. When for a specific feature multiple preferred ranges are described in the format "from x to y", it is understood that all ranges combining the different endpoints are also contemplated. The disclosure of the invention as found herein is to be considered to cover all embodiments as found in the claims as being multiply dependent upon each other irrespective of the fact that claims may be found without multiple dependency or redundancy.

DETAILED DESCRIPTION OF THE INVENTION

The present invention provides for a novel silicone compound of the formula:

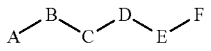

The units of block E may be cross-linked with another series of block E through R3 to form a net like architecture of the general formula:

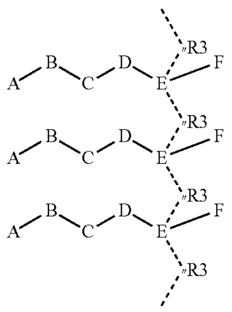

In a compound of the hydroxyanthraquinone group depicted above, usually, only one of the hydroxyl groups reacts with the polymer chain. The various forms of hydroxyanthraquinone are as shown below:

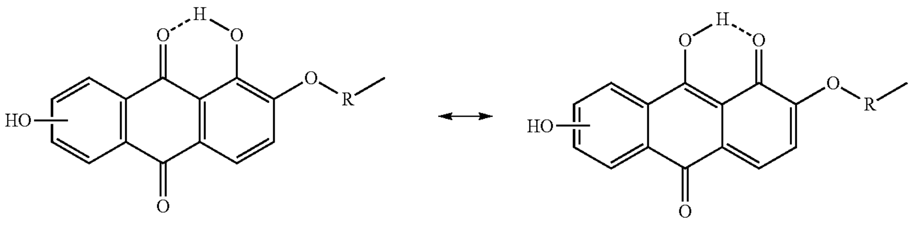

R is a difunctional organic moiety covalently connecting the hydroxyanthraquinone chromophore and polymer chain.

The Difunctional Spacer Group (R3)

R3 is an organic moiety (or spacer) containing carbon, nitrogen, phosphorous, sulphur, oxygen or silicon atoms. The difunctional spacer group has two terminal alkenyl or alkynyl groups. The base silicone polymer chains are covalently linked to each other through difunctional spacer groups.

These difunctional spacer groups prevent excessive and three dimensional cross-linking, which leads to a gelled mass. Instead they help in forming a cross-linked elastomeric compound that is relatively easier to incorporate in personal care compositions. The difunctional spacer group is preferably of the formula:

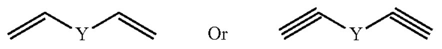

where Y is organic moiety containing carbon, nitrogen, phosphorous, sulphur, oxygen or silicon atoms.

The difunctional spacer compound is preferably selected from the group consisting of dialkenyl polyethers, alpha omega dienes, alpha omega diynes; alpha omega ene-ynes or di alkenyl and dialkynyl terminated polysiloxane. Suitable examples of alpha omega-dienes are 1,4-pentadiene, 1,5-hexadiene, 1,7-octadiene; 1,8-nonadiene, 1,9-decadiene, 1,11-dodecadiene, 1,13-tetradecadiene and 1,19-eicosadiene. Suitable examples of alpha omega-diynes are 1,3-butadiyne or 1,5-hexadiyne, whereas alpha omega ene-yne is preferably hexene-5-yne. It is further preferred that the spacer groups are siloxane or polyether based.

Di-alkenyl terminated polysiloxanes are preferably of the general formula:

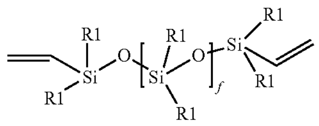

wherein f is an integer 1-10,000. More preferably the number of repeat units are in the range of 300-500 corresponding to an average molecular weight in the range of 22,000-40,000 Daltons. A vinyl terminated polysiloxane having 375 repeat units and molecular weight of 28,000 Daltons is particularly preferred.

The di-alkenyl terminated polyethers can be represented by the following general formula:

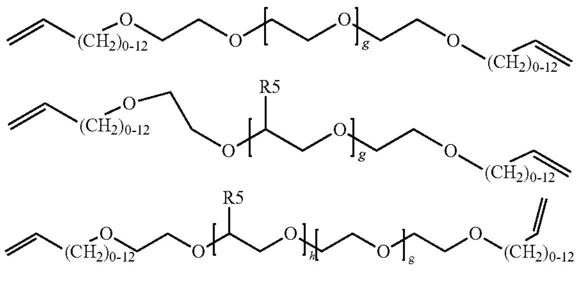

R5 is R1 or —H; wherein g and h are an integer 1-10,000.

Units A and F

Units A and F are the terminal moieties. In the units A and F, the functional R1 is preferably methyl or ethyl.

Blocks B, C, D and E

Blocks B, C, D, and E are non-terminal moieties independently positioned between A and F in any order. Thus the order may be B—C-D-E as shown in the formula in the summary of the invention, or the order could be any permutation and combination which satisfies the rule "independently positioned between A and F in any order" i.e. it may be B-D-C-E, B—C-E-D, D-C-E-B, and a host of other possibilities.

Process

The invention also provides for a convenient process to prepare the silicone compound of the invention.

In the process of the invention, the Si—H containing siloxane is of the general formula:

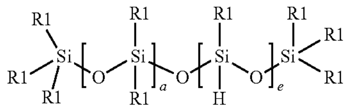

where e is an integer 1-10,000.

The Si—H containing siloxane is preferably present in 0.001 to 95% by weight of the reaction mixture.

The uv-visible absorbing moiety (Vi) is selected from a hydroxyanthraquinone compound. The term "uv-visible absorbing moiety" as used herein means a moiety having a molar extinction coefficient of at least 50 units.

The compound of the formula:

$Vi\text{-}O—(CH_2)_{0\text{-}50}—CH═CH_2$ or $CH_2═CH—(CH_2)_{0\text{-}50}\text{-}Vi\text{-}O—(CH_2)_{0\text{-}50}—CH═CH_2$ or $Vi\text{-}O—(CH_2)_{0\text{-}50}—C≡CH$ or $CH≡C—(CH_2)_{0\text{-}50}\text{-}Vi\text{-}O—(CH_2)_{0\text{-}50}—C≡CH$ is preferably present in 0.001 to 95% by weight of the reaction mixture.

The difunctional spacer compound used in the process of the invention preferably has the formula

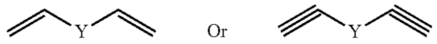

where Y is organic moiety containing carbon, nitrogen, phosphorous, sulphur, oxygen or silicon atoms. Y is preferably a compound selected from a group consisting of hydrocarbons, polysiloxanes, polyethers, polycarboxylic acids, or polysaccharides. The difunctional spacer compound is preferably present in 0.001 to 95% by weight of the reaction mixture.

The process is preferably carried out in the presence of a monofunctional organic moiety of the general formula

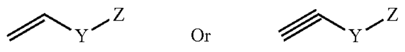

where z is —R1 or —OH or —H. The monofunctional organic moiety is preferably present in 0.001 to 95% by weight of the reaction media.

The compounds most preferred for providing the functionality of block C are Polyethylene Glycol Monoallyl Ethers (Clarient) and long chain alkenes such as octadecene (Sigma Aldrich) having general structure indicated below:

Polyethylene Glycol Monoallyl Ethers

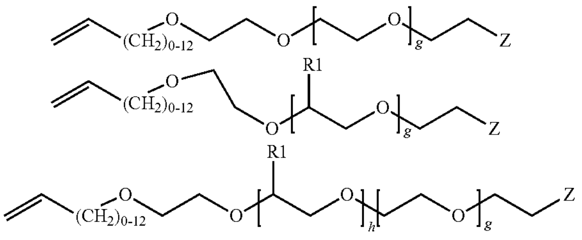

Long Chain Alkenes

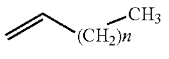

n = 1-30 or

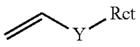

Or

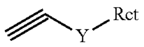

where Rct is reactive group containing carbon, nitrogen, phosphorous, sulphur, oxygen or silicon atoms. Alternately, the monofunctional organic moiety is preferably of a general formula:

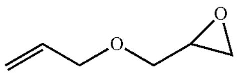

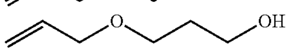

Block C has been found to be useful to include in the compound of the invention since it can be selected to provide useful properties like emulsification and act as a solubilizer for other oleophilic materials like sunscreens. Also, when used in hair care products, this has been found to be effective in deposition of actives to hair through water based wash off or rinse systems.

Catalyst

The reaction is carried out in the presence of a catalyst. The catalyst is preferably selected from metal complexes or their compounds or metals in free or immobilized form. Transition metals such as platinum, palladium and rhodium are particularly preferred. Preferred catalysts include chloroplatinic acid, complexes of platinum with unsaturated compounds e.g. platinum(0)-1,3-divinyl-1,1,3,3-tetramethyldisiloxane complex; platinum(0)-2,4,6,8-tetramethyl-2,4,6,8-tetravinylcyclotetrasiloxane complex; Pt0(1,5 cyclooctadine) i.e. Pt(COD)]; platinum phosphine complexes; platinum on carbon; platinum on inorganic supports such as silica and platinum black. Complexes of other metals such as palladium, rhodium may also be used for the reaction, for example, Wilkinson's catalyst $RhCl[(C6H5)P]_3$. The catalyst can be in heterogeneous phase e.g. on charcoal or, preferably, in homogeneous phase (Karstedt catalyst). Platinum(0)-1,3-divinyl-1,1,3,3-tetramethyldisiloxane complex is most preferred catalyst. The catalyst is preferably used in an amount of 0.0001 to 20% by weight of the reaction mixture.

Reaction Media

The reaction is carried out in the presence of a reaction media which is a solvent which is water, a silicone fluid, polar organic compound, a non-polar organic compound or mixtures thereof. Typically the solvent is present in an amount of 0. 1 to 99.89 weight % based on the weight of all ingredients in the reaction mixture. Preferably the solvent is present in an amount of from 1 to 80 weight % and more preferably from 1 to 50 weight %. When the solvent is a polar or non-polar organic compound, it is preferred that the amount to be used is that which would create a product containing <40 weight % solids. When used, the solvent becomes an integral part of the resulting elastomer composition and affects the structural and physical properties of the silicone elastomer. Preferably the solvent is not removed from the silicone elastomer composition. Silicone fluid useful as the solvents include, alkyl and/or aryl siloxanes. Preferred are volatile methyl siloxanes (VMS).

Linear VMS have the Formula

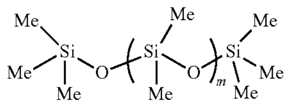

m = 1-100

Cyclic VMS have the Formula

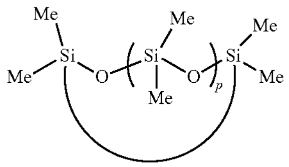

p = 1-10

Preferably the volatile methyl siloxane have a normal boiling point less than about 250° C. Representative linear volatile methyl siloxanes include, but are not limited to hexamethyldisiloxane, octamethyltrisiloxane, decamethyltetrasiloxane, dodecamethylpentasiloxane, tetradecamethylhexasiloxane, and hexadecamethylheptasiloxane. Representative cyclic volatile methyl siloxanes are hexamethylcyclotrisiloxane, octamethylcyclotetrasiloxane, decamethylcyclopentasiloxane, and dodecamethylcyclohexasiloxane. Representative branched volatile methyl siloxanes are heptamethyl-3-{(trimethylsilyl)oxy}trisiloxane, hexamethyl-3,3,bis{(trimethylsilyl)oxy}trisiloxane, and pentamethyl {(trimethylsilyl)oxy}cyclotrisiloxane.

Illustrative of such silicone fluids are polydimethylsiloxane, polydiethylsiloxane, polymethylethylsiloxane, polymethylphenylsiloxane, and polydiphenylsiloxane. Organofunctional silicone fluids can also be employed as the solvent. Examples of functional silicone fluids include, but are not limited to, acrylamide functional silicone fluids, acrylate functional silicone fluids, carbinol functional silicone fluids, carboxy functional silicone fluids, chloroalkyl functional silicone fluids, glycol functional silicone fluids, ketal functional silicone fluids, mercapto functional silicone fluids, methyl ester functional silicone fluids, perfluoro functional silicone fluids, polyisobutylene (PIB) functional silicone fluids, silanol functional silicone fluid, and vinyl functional silicone fluids. When silicone fluids are used, the resulting ultraviolet radiation absorbing silicone compound is in the form of silicone gels.

Non-polar organic compounds may also be used as the solvents. The commonly used organic solvents include aromatic hydrocarbons, aliphatic hydrocarbons, high molecular weight alcohols, aldehydes, ketones, amines, esters, ethers, glycols, glycol ethers, alkyl halides, or aromatic halides. When a polar or non-polar organic solvent is used, the resulting silicone compound is in the form of a silicone gel. Suitable organic solvents are the ones that do not undergo a chemical reaction with any of the components of the silicone phase, under the anticipated conditions of processing and use and that is suitable for use in the intended end-use application.

The reaction temperature, depending upon the reactants, is in the range of 0-250° C. and preferably about 80-120° C. and most preferably about 110° C. The reaction time may vary between 1 minute to about 48 hours, more preferably between 1 to 12 hours.

Swelling Agent

After the reaction is taken to desired completion, the contents are then preferably added to a swelling agent. The swelling agent is preferably a solvent hereinabove described with the exception of water or low molecular weight alcohols. Thus the swelling agent may be a silicone fluid, a polar organic compound, or a non-polar organic compound with the above exceptions. The swelling agent is most preferably a silicone fluid or a functional silicone fluid. The swelling agent is preferably used in an amount which is in a weight ratio of 1:10 to 10:1, more preferably 1:1 to 5:1 with respect to the reaction mixture.

An additional advantage of the present invention is that the silicone compound of the invention can be used as a delivery vehicle for active ingredients such as oil soluble vitamins, fragrances and sunscreens. Fragrance oils that are compatible with silicone elastomers can be absorbed into the silicone compound of the invention and their volatility will be reduced, thereby improved the desired sensorial impact.

An advantage of the present invention is that the silicone compound of the invention when incorporated in sunscreen compositions comprising well known UV-A organic sunscreens and oil-soluble UV-B sunscreens synergistically boosts the sun-protection factor (SPF). Preferred UV-A sunscreen for getting this benefit is Parsol 1789. Preferred oil soluble UV-B sunscreen for getting this benefit is selected from the class of cinnamic acid, salicylic acid, diphenyl acrylic acid or derivatives thereof. Examples of such oil-soluble organic sunscreens are Octisalate™, Homosalate™, NeoHelipan™, Octocrylene™ or Parsol MCX™. Most suitable oil-soluble UV-B organic sunscreen is Parsol MCX.

Preferred Reaction Scheme

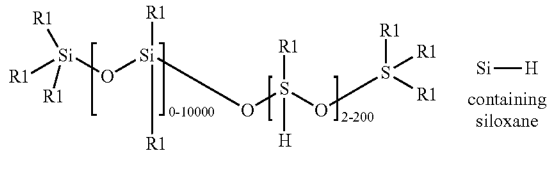

+

-continued

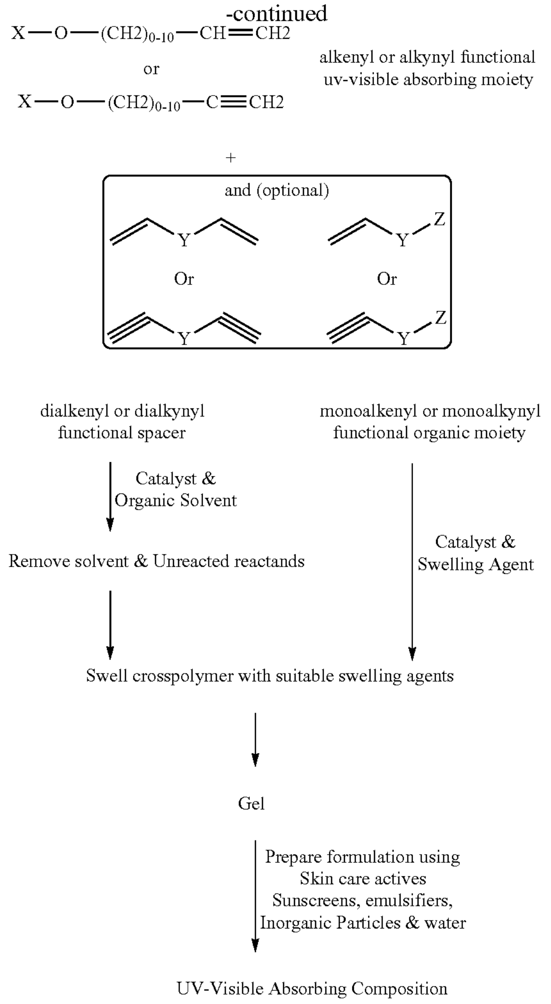

Personal Care Composition

"Personal Care Composition" as used herein, is meant to include a composition for topical application to skin and/or hair of mammals, especially humans. Such a composition may be generally classified as leave-on or rinse off, and includes any product applied to a human body for improving appearance, cleansing, odor control or general aesthetics. The composition of the present invention can be in the form of a liquid, lotion, cream, foam, scrub, gel, soap bar or toner, or applied with an implement or via a face mask, pad or patch. Non-limiting examples of personal care compositions include leave-on skin lotions and creams, shampoos, conditioners, shower gels, toilet bars, antiperspirants, deodorants, dental products, shave creams, depilatories, lipsticks, foundations, mascara, sunless tanners and sunscreen lotions. "Skin" as used herein is meant to include skin on the face and body (e.g., neck, chest, back, arms, underarms, hands, legs, buttocks and scalp).

According to yet another aspect, the present invention relates to a personal care composition comprising the silicone compound according to the invention, in a cosmetically acceptable vehicle. It is preferred that the compound is present from 1 to 30% by weight of the composition, more preferably from 2 to 15%, and most preferably from 3 to 10% by wt of the composition. These are suitable for the protection of human skin and/or hair from damaging effects of UV radiation.

The personal care compositions of the invention are useful as compositions for photo protecting the human epidermis or hair against the damaging effect of UV irradiation, as antisun/sunscreen composition or as makeup product. Such compositions can, in particular, be provided in the form of a lotion, a thickened lotion, a gel, a cream, cleansing milk, an ointment, a powder or a solid tube stick and may optionally be packaged as an aerosol and may be provided in the form of a mousse, foam or a spray.

The personal care compositions of the invention can also contain usual cosmetic adjuvants and skin care additives commonly employed in skin care products such as liquid or solid emollients, silicone oils, emulsifiers, solvents, humectants, polymeric or inorganic thickeners, powders, pigments (example clay mineral, barium sulfate, or pearl pigments, for example silver or gold, or any iris foil pearl pigment, having an interference color of red, orange, green, blue, or, purple (including any iris foil pearl pigments covered with inorganic pigments, organic pigments, laked pigments, etc.), bismuth oxychloride, bismuth oxychloride coated mica), organic or inorganic sunscreens with and without photostabiliser, skin lightening agents, skin conditioners, optical brighteners, propellants, healing agents (example allantoin), cooling agents (example urea, menthol, menthyl lactate, frescolate), antiseptic agents and other specific skin-benefit actives, skin care actives such as skin lightening actives, antiaging, antiacne, antibacterials, antiperspirant agents etc. The vehicle may also further include adjuncts such as antioxidants, perfumes, opacifiers, preservatives, colorants and buffers. The necessary amounts of the cosmetic and dermatological adjuvants and additives, based on the desired product, can be chosen by the skilled person.

The composition may additionally comprise from 0.1 to 20%, more preferably from 0.1 to 5% of an inorganic sunscreen agent. Inorganic sunscreens, which may be employed, are for e.g. titanium dioxide, zinc oxide or silica such as fumed silica and mixtures thereof. These are preferably in the micronized form. Ultrafine titanium dioxide in either of its two forms, namely water-dispersible titanium dioxide and oil-dispersible titanium dioxide, may be suitable for the invention. Water-dispersible titanium dioxide is ultra-fine titanium dioxide, the particles of which are non-coated or which are coated with a material to impart a hydrophilic surface property to the particles. Examples of such materials include aluminium oxide and aluminium silicate. Oil-dispersible titanium dioxide is ultrafine titanium dioxide, the particles of which exhibits a hydrophobic surface property, and which, for this purpose, can be coated with metal soaps such as aluminium stearate, aluminium laurate or zinc stearate, or with organosilicone compounds. By "ultrafine or micronized form" is meant particles of inorganic sunscreens having an average particle size of less than 100 μm, preferably 70 μm or less, more preferably less than 40 μm and most preferably from 15 to 25 μm.

Vitamins, which act as skin-lightening ingredients can be advantageously included in the composition to provide for additional skin lightening effects. These include vitamin B3, vitamin B6, vitamin C, vitamin A or their precursors and cosmetically acceptable derivatives. Mixtures of the vitamins can also be employed in the composition of the invention. When present, these vitamins are used in the range of 0.01 to 10.0% by weight of said composition.

Emollients, such as stearyl alcohol, glyceryl monoricinoleate, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, eicosanyl alcohol, behenyl alcohol, cetyl palpitate, silicone oils such as dimethylpolysiloxane, organomodified silicones such as cetyl dimethicone, steryl dimethicones; cross-linked silicone elastomers/resins; organomodified cross-linked silicone elastomers/resins di-n-butyl sebacate, isopropyl myristate, isopropyl palmitate, isopropyl stearate, butyl stearate, polyethylene glycol, triethylene glycol, lanolin, cocoa butter, corn oil, cotton seed oil, olive oil, palm kernel oil, rape seed oil, safflower seed oil, evening primrose oil, soybean oil, sunflower seed oil, avocado oil, sesame seed oil, coconut oil, arachis oil, castor oil, acetylated lanolin alcohols, petroleum jelly, mineral oil, butyl myristate, isostearic acid, palmitic acid, isopropyl linoleate, lauryl lactate, myristyl lactate, decyl oleate, myristyl myristate; Propellants, such as propane, butane, isobutane, dimethyl ether, carbon dioxide, nitrous oxide; Solvents, such as ethyl alcohol, isopropanol, acetone/ethylene glycol monoethyl ether, diethylene glycol monobutyl ether, diethylene glycol monoethyl ether; Powders, such as chalk, talc, fullers earth, kaolin, starch, gums, colloidal silica sodium polyacrylate, tetra alkyl and/or trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, ethylene glycol monostearate; Plant extracts such as those from genus *Rubia, Symplocus, Curcuma* and various perfume/fragrance ingredients may also be included in the composition at ranges from 0.001 to 40.0% by weight of the composition. The emollient is preferably present in an amount from about 1 to about 20%, preferably about 2 to about 15%, and most preferably about 4 to about 10% by weight of the total weight of the composition.

The preservatives and antioxidants are preferably present in an amount ranging about 0.01 to about 10% of the total weight of the composition. Preferably the preservatives and/or antioxidants are present in an amount varying about 0.1 to about 1% by weight.

Preferred emulsifiers that may be used to form O/W, W/O is and/or O/W/O formulations, include sorbitan oleate, sorbitan sesquioleate, sorbitan isostearate, sorbitan trioleate, polyglyceryl-3-diisostearate, polyglycerol esters of oleic/isostearic acid, polyglyceryl-6 hexaricinolate, polyglyceryl-4-oleate, polygylceryl-4 oleate/PEG-8 propylene glycol cocoate, oleamide DEA, TEA myristate, TEA stearate, magnesium stearate, sodium stearate, potassium laurate, potassium ricinoleate, sodium cocoate, sodium tallowate, potassium castorate, sodium oleate, silicone based emulsifiers and mixtures thereof.

The oily phase of the compositions according to the present invention may also contain natural vegetable or animal waxes such as bee wax, china wax, bumblebee wax and other waxes of insects as well as shea butter.

The aqueous phase of the formulations of the present invention may contain the usual cosmetic additives such as alcohols, especially lower alcohols, preferably ethanol and so or isopropanol, low alkyl diols or polyols and their ethers, preferably propyleneglycol, glycerine, ethyleneglycol, ethylene glycol monoethyl or monobutyl ether, electrolytes and especially, one or more thickeners. Thickeners that may be used in formulations of the present invention include the family of silicon dioxide, magnesium and/or aluminum silicates, polysaccharides and their derivatives such as hyaluronic acid, xanthan gum, hydroxypropyl cellulose, acrylate copolymers, preferably a polyacrylate of the family of carbopols, such as carbopols of type 980, 981, 1382, 2984, 59S4.

Moisturizing agents, such as humectants, may be incorporated into the compositions according to the present invention to reduce the trans-epidermal water loss (TEWL) of the horny layer of the skin. Suitable humectants include glycerin, lactic acid, pyrrolidone carbonic acid, urea, polyethylene glycol, polypropylene glycol, sorbitol, PEG-400, and mixtures thereof. Additional suitable moisturizers are polymeric moisturizers of the family of water soluble and/or with water gelating polysaccarides such as hyaluronic acid, chitosan and/or fucose rich polysaccharides available, e.g. as Fucogel1000 (CAS-Nr. is 178463-23-5) from SOLABIA S. The moisturizing agent is optionally present in an amount about 0.5 to about 8%, preferably about 1 to about 5% by weight of the total weight of the composition.

Suitable neutralizing agents which may be included in the composition of the present invention to neutralize components such as e.g. an emulsifier or a foam builder/stabilizer include but are not limited to alkali hydroxides such as a sodium and potassium hydroxide) organic bases such as diethanolamine (DEA), triethanolamine (TEA), aminomethyl propanol, trisodium ethylenediaminetetraacetic acid and mixtures thereof; basic amino acids such as arginine and lysine and any combination of any of the foregoing. The neutralizing agent may be present in an amount of about 0.01 to about 8% by weight in the compositions of the present invention, preferably 1 to about 5% by weight. The addition of electrolytes into the composition of the present invention may be necessary to change the behavior of a hydrophobic emulsifier. Thus the emulsions may preferably contain electrolytes of one or several salts including anions such as a chloride, a sulfate, a carbonate, a borate or an aluminate, without being limited thereto. Other suitable electrolytes may be on the bases of organic anions such as, but not limited to, lactate, acetate, benzoate, propionate, tartrate and citrate. As cations preferred are ammonium, alkyl ammonium, alkaline or alkaline earth metals such as Sodium or Magnesium. Especially preferred salts are potassium and sodium chloride, magnesium sulfate, zinc sulfate and mixtures thereof. Electrolytes are preferably present in an amount of about 0.01 to about 0.5% by weight in the compositions of the present inventions.

The invention will now be explained in detail with help of the following non-limiting examples, which form preferred embodiments of the various aspects of the invention.

EXAMPLES

Example 1

Synthesis of Ultraviolet-visible Light Absorbing Linear Silicone Polymer Compound Having Alizarin Moiety This silicone compound was synthesized in three stages.

Stage 1: Synthesis of allyloxy functional alizarin derivative (a compound of the formula Vi-O—$(CH_2)_{0\text{-}50}$—CH═$CH_2$ or Vi-O—$(CH_2)_{0\text{-}50}$—C≡CH i.e. component (ii) of the process of the invention.)

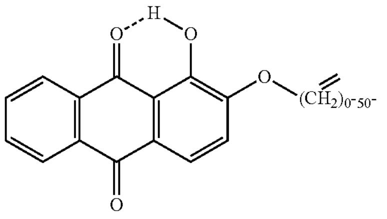

or

-continued

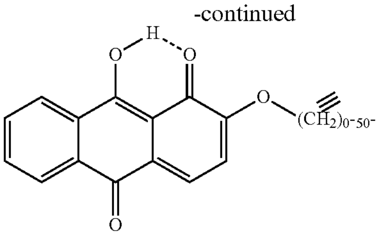

Stage 2: Synthesis of methylhydrogenpolysiloxane (MHPS) copolymer (Si—H containing siloxane of component (i) of the process of the invention).

Stage 3: Hydrosilylation.

Stage 1: Synthesis of Allyloxy Functional Alizarin Derivative

A 2-liter, 3-necked flask was fitted with condenser and additional funnel. The flask was charged with 5 g (0.014 mol) of alizarin and 17.7 ml of ethanol. Sodium ethoxide 2.268 g (0.042 mol) as a 21% solution in ethanol was added rapidly. The mixture was heated to 50-60° C. for 2 hours. Allyl bromide (3.7 g; 0.042 mol) was added and the mixture heated to reflux (70-74° C.) for 20 hours. The mixture was allowed to return to room temperature and 50 ml water were added, followed by 17 ml of toluene and about 1 ml of 38% aqueous hydrochloric acid. The organic layer was separated and washed with 50 ml of water. Volatiles were removed from the organic layer by rotary evaporation at 80° C. and at 2 mm Hg to give 5 g of allyl ether intermediate.

A dark brownish yellow coloured sticky solid was obtained having, 1H-NMR (CDCl3) peaks (due to allyl and methoxy group present on alizarin molecule) at 6.05 (m, 1H, CH2═CH—CH2-O—), 5.32 and 5.43 (2H, CH2═CH—CH2-O), 4.6 (2H, CH═CH2-CH2-O), 3.9 (3H, CH3O—).

Stage 2: Synthesis of Methylhydrogen-Polysiloxane (MHPS) Copolymer 50 g of octamethycyclotetrasiloxane ($D_4$) was mixed with 15 g of methylhydrogen-polysiloxane (Aldrich, MHPS) in a two necked round bottom flask. To the mixture 1 g of Tulsion catalyst (Thermax, T63MP) was added. The reaction mixture was stirred at 120° C. for 4 hours. Viscous MHPS copolymer obtained was cooled down to room temperature. Catalyst was filtered off. Unreacted $D_4$ was distilled off under vacuum at 125° C. The product obtained was a colourless and viscous oily substance.

The colorless and viscous oily substance was characterised with an FTIR peak due to Si—H at 2115 $cm^{-1}$, Si—$CH_3$ at 1260 $cm^{-1}$, —Si—O—Si at 1186 $cm^{-1}$; $^1$H-NMR ($CDCl_3$) peaks at δ 0.09 (s, Si$\underline{CH_3}$), 0.17 (s, Si($\underline{CH_3}$)H) and 4.68 (s, Si—$\underline{H}$).

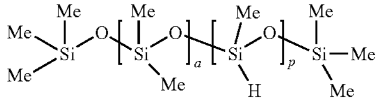

MHPS copolymer

MHPS Copolymer

Stage 3: Hydrosilylation 100 ml toluene were charged to a 3-necked flask fitted with a Dean and Stark set-up under nitrogen atmosphere. Traces of water present in toluene were removed by azeotropic distillation. 1.5 g allyloxy functional alizarin class (as prepared in stage 1 above) were charged into a moisture-free 3-necked flask, fitted with as reflux assembly, maintained under nitrogen atmosphere. 50 ml dry toluene was added subsequently to dissolve all the reagents. One drops of platinum catalyst (1,3-divinyltetramethyldisiloxane, Sigma-Aldrich) were added to the reaction mixture and the mixture was stirred at room temperature for about 0.5 hours. 2 g of methylhydropolysiloxane (MHPS) copolymer (as prepared in stage 2 above) was added and the reaction was stirred at about 110° C. for about 2-3 hours. The progress of the reaction was monitored by TLC and FT-IR. The product was obtained in a polymer form. The polymer was further washed with methanol to remove unreacted organic matter and platinum catalyst. The remaining traces of toluene and methanol were removed under vacuum below 60° C.

The in-vitro absorbance of a 500 ppm solution of the compound obtained in example 1 showed two UV absorption maxima, one at 310 nm with an absorbance value of 0.65 units and the other at 355 nm with a corresponding absorbance value of 0.80 and at 440 nm with a corresponding absorbance value of 0.26 units, thereby confirming the presence of both the UV as well as visible absorbing moieties.

Thus it can be readily seen that the compound of the present invention provides protection against both UV and visible radiation as indicated by absorbance in UVA, UVB and visible radiation wavelengths and the compound exhibits high photostability.

Quantification of Photostability via Transmittance Study

The composition of example 1 was applied on a transpore tape (3M) which was fixed to the quartz plate. The application was performed using transpore tape as the substrate fixed over quarts plate. The amount of cream applied was 3 mg/$cm^2$. The intensity of simulated solar atlas lamp sun lamp was 5.5 mW/$cm^2$. The quartz plate was dried and kept in the solar simulator. The transmitted energy was measured through the film present on the transpore tape/quartz, using radiometer. The % transmission (% T) at 350, 400, 450 nm were recorded at zero time of solar simulated sun light exposure. Next, this polymer film was exposed to solar simulated sun light for 30, 60 and 120 minutes respectively. The % T at 350, 400, 450 nm were recorded after 30, 60 and 120 minutes of solar simulated sun light exposure. The transmitted energy obtained from the transpore tape/quartz was used as the control.

TABLE 1

| | % Transmittance | | |
|---|---|---|---|
| Compound prepared in Example 1 | 350 nm | 400 nm | 450 nm |
| Before UV exposure | 10 | 10 | 10 |
| Before 30 minutes of UV exposure | 5 | 5 | 5 |
| Before 60 minutes of UV exposure | 5 | 5 | 5 |
| Before 120 minutes of UV exposure | 5 | 5 | 5 |

The data in table 1 indicates that compound of the invention is photostable over time on UV-Vis light exposure.

Example 1A

Admixture of MHPS (Linear Polymer) and Alizarin

Alizarin (at 10% by weight of the composition) was mixed with methylhydropolysiloxane (MHPS) copolymer (as prepared in stage 2 above) to obtain a composition of comparative example 1A. The appearance of the polymer composition (example 1A) obtained by physical addition of alizarin to the polymer was opaque and not homogeneous where particles of alizarin could be seen to be physically dispersed in the gel matrix when observed under microscope. On the other hand, the appearance of the polymer of example 1 where alizarin is covalently attached to silicone backbone was transparent and homogeneous and no particles could be seen when observed under microscope. Thus, the composition of example 1A does not provide for uniform distribution of alizarin in the polymer thereby affording poor UV visible protection.

Transmittance Study

The compositions of example 1 and example 1A were applied on a transpore tape (3M) which was fixed to the quartz plate. The application was performed using transpore tape as the substrate fixed over quarts plate. The amount of cream applied was 3 mg/$cm^2$. The intensity of simulated solar atlas lamp sun lamp was 5.5 mW/$cm^2$. The quartz plate was dried and kept in the solar simulator. The transmitted energy was measured through the film present on the transpore tape/quartz, using radiometer. The transmitted energy obtained from the transpore tape/quartz was used as the control.

TABLE 2

| | % Transmittance | | |
|---|---|---|---|
| Examples | 350 nm | 400 nm | 450 nm |
| Example 1 | 10 | 10 | 12 |
| Example 1A | 20 | 22 | 22 |

The data in table 2 indicates that composition as per the invention (example 1) provides for excellent UV-Vis protection as evidenced by the low transmission values.

Example 2

Synthesis of Ultraviolet Visible Light Absorbing Silicone Compound (Silicone Elastomer Gel) Having Alizarin Moiety This silicone compound was synthesized in four stages.

Stage 1: Synthesis of allyloxy functional alizarin derivative (a compound of the formula Vi-O—$(CH_2)_{0-50}$—CH═$CH_2$ or Vi-O—$(CH_2)_{0-50}$—C≡CH i.e. component (ii) of the process of the invention.)

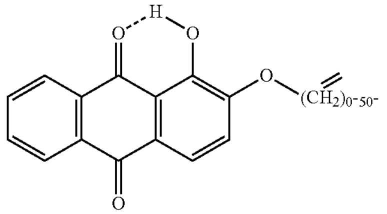

or

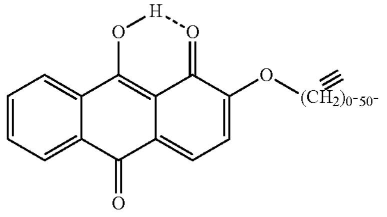

Stage 2: Synthesis of methylhydrogenpolysiloxane (MHPS) copolymer (Si—H containing siloxane of i.e. component (i) of the process of the invention).

Stage 3: Synthesis of divinyl terminated polysiloxane copolymer (VTP) spacer (a difunctional spacer compound having alkenyl or alkynyl group to enable formation of crosslinked gel.

Stage 4: Hydrosilylation and Swelling

Stage 1: Synthesis of Allyloxy Functional Alizarin Derivative

The compound was prepared as in example 1.

Stage 2: Synthesis of Methylhydrogen-Polysiloxane (MHPS) Copolymer

The copolymer was synthesized as in example 1.

Stage 3: Synthesis of Divinyl Terminated Polysiloxane (VTP) Copolymer 20 g of octamethycyclotetrasiloxane ($D_4$) was mixed with 4 g of divinyltetramethyldisiloxane (Aldrich) in a 50 ml 2-necked flask. To the mixture 0.3 g of Tulsion catalyst (Thermax, T63MP) was added. The reaction mixture was stirred at 120° C. for 4 hours. Divinyl terminated polysiloxane copolymer (VTP) copolymer obtained was cooled down to room temperature. Catalyst was filtered off. Unreacted $D_4$ was distilled off under vacuum at 125° C. The product obtained was colorless viscous oil. This was used as the spacer compound.

The colorless, viscous liquid was characterised with $^1$H-NMR ($CDCl_3$) peaks at δ 0.09 (s, $Si\underline{CH_3}$), 0.17 (s, $Si(\underline{CH_3})H$), 0.8 (m, $Si—\underline{CH}═CH_2$), 5.6-6.2 (s, $Si—CH═\underline{CH_2}$).

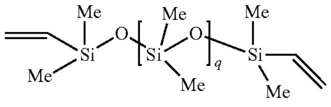

Divinyl terminated polysiloxane (VTP) copolymer

Divinyl Terminated Polysiloxane (VTP) Copolymer

Stage 4: Hydrosilylation and Swelling 100 ml toluene were charged to a 3-necked flask fitted with a Dean and Stark set-up under nitrogen atmosphere. Traces of water present in toluene were removed by azeotropic distillation. 1.5 g allyloxy functional alizarin (as prepared in stage 1 above) and 0.21 g divinyl terminated polysiloxane (VTP) (as prepared in stage 3 above) were charged into a moisture-free 3-necked flask, fitted with a reflux assembly, maintained under nitrogen atmosphere. 50 ml dry toluene was added subsequently to dissolve all the reagents. One drop of platinum catalyst (1,3-divinyltetramethyldisiloxane, Sigma-Aldrich) were added to the reaction mixture and the mixture was stirred at about 25° C. for about 0.5 hours. 2 g of methylhydropolysiloxane (MHPS) copolymer (as prepared in stage 2 above) was added and the reaction was stirred at about 110° C. for about 2-3 hours. The progress of the reaction was monitored by TLC and FT-IR. The product was obtained in a gel form. The gel was further washed with methanol to remove unreacted organic matter and platinum catalyst. It was further swollen in 30 g of (decamethylcyclopentasiloxane) $D_5$ and remaining traces of toluene and methanol were removed under vacuum below 60° C.

The in-vitro absorbance of a 500 ppm solution of the compound obtained in example 2 showed two UV absorption maxima, one at 310 nm with an absorbance value of 0.65 units and the other at 355 nm with a corresponding absorbance value of 0.80 and at 440 nm with a corresponding absorbance value of 0.26 units, thereby confirming the presence of both the UV as well as visible absorbing moieties.

Thus it can be readily seen that the preferred compound (crosslinked elastomer gel) of the present invention provides protection against both UV and visible radiation as indicated by absorbance in UVA, UVB and visible radiation wavelengths.

Example 2A

Admixture of Commercial Gel and Alizarin

Alizarin (at 10% by weight of the composition) was mixed with Silicone 9040 gel (Dow Corning®) to obtain a composition of comparative example 2A. The appearance of the gel composition (example 2A) obtained by physical addition of alizarin to the gel was opaque and not homogeneous where particles of alizarin could be seen to be physically dispersed in the gel matrix when observed under microscope. On the other hand, the appearance of the gel of example 2 where alizarin is covalently attached to silicone backbone was transparent and homogeneous and no particles could be seen when observed under microscope. Thus, the composition of example 2A does not provide for uniform distribution of alizarin in the polymer thereby affording poor UV visible protection.

Transmittance Study

The compositions of example 2 and example 2A were applied on a transpore tape (3M) which was fixed to the quartz plate. The application was performed using transpore tape as the substrate fixed over quarts plate. The amount of cream applied was 3 mg/cm$^2$. The intensity of simulated solar atlas lamp sun lamp was 5.5 mW/cm$^2$. The quartz plate was dried and kept in the solar simulator. The transmitted energy was measured through the film present on the transpore tape/quartz, using radiometer. The transmitted energy obtained from the transpore tape/quartz was used as the control. The data is summarized in table 3 below.

TABLE 3

| | % Transmittance | | |
|---|---|---|---|
| Examples | 350 nm | 400 nm | 450 nm |
| Example 2 | 40 | 30 | 40 |
| Example 2A | 70 | 70 | 70 |

Example 3

Personal Care Composition Comprising the Crosslinked Elastomer Gel Silicone Compound of the Invention A personal care composition was prepared using the silicone compound of the invention. First the ingredients were prepared in two different phases i.e. (i) an oil phase and (ii) a water (aqueous) phase. The ingredients in the respective phases are tabulated below in table 4.

TABLE 4

| Ingredients | % by weight in the composition |
|---|---|
| Compound prepared in example 2 | 50 |
| Emulsifier 5225C | 20 |
| Titanium dioxide | 0.9 |
| Water | To 100 |

Compound prepared in example 1 was mixed with Emulsifier 5225C and homogenized for 10 minutes. $TiO_2$ was added and mixture was homogenized for 10 minutes. Water was added slowly until under homogenization until a smooth cream with acceptable spreading characteristics was obtained.

The invention claimed is:

1. A silicone compound of the general formula:

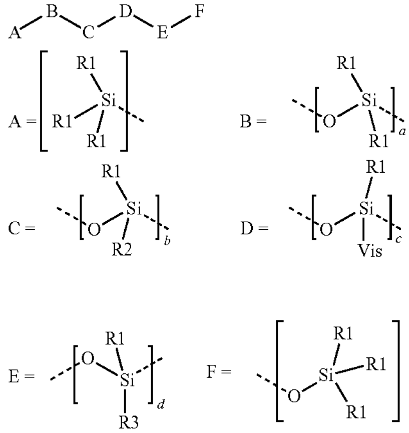

where each R1 is independently a straight or branched alkyl, cycloalkyl, polycycloalkyl, heterocycloalkyl, alkaryl, alkoxy, aryl, aralkyl, alkenyl, alkynyl or fluorocarbon group containing 1-50 carbon atoms;

R2 is R1 or —H, —OH or an organic moiety containing carbon, nitrogen, phosphorous, sulphur, oxygen or silicon atoms;

"Vis" is a UV-visible absorbing moiety selected from the hydroxyanthraquinone group

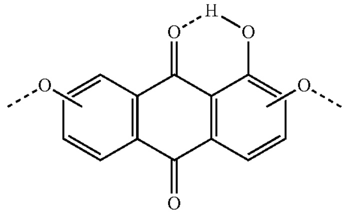

which is capable of covalently linking to a polymer chain;

R3 is R1 or optionally an organic moiety or spacer containing carbon, nitrogen, phosphorous, sulphur, oxygen or silicon atoms capable of linking to another polymer;

units A and F are the terminal moieties;

blocks B, C, D and E are non-terminal moieties independently positioned between A and F in any order;

a and c are each independently integers 1-10 000; and b and d are each independently an integer 0-10 000.

2. A compound as claimed in claim 1 wherein the units of block E are cross-linked with another series of units of block E through R3 to form a net-like architecture of the general formula:

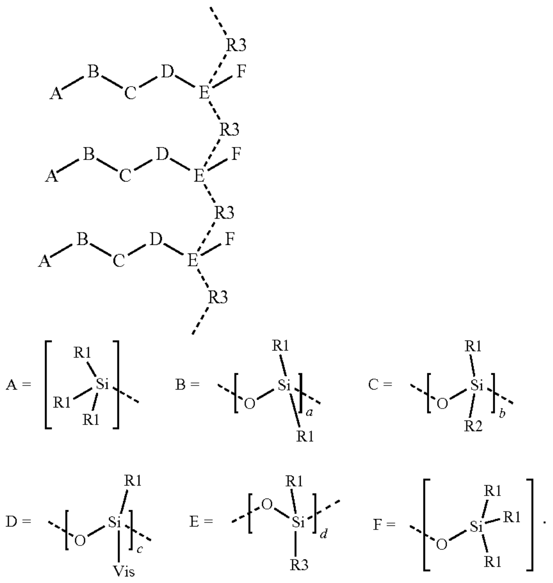

3. A process for the preparation of a silicone compound as claimed in claim 1 comprising the steps of reacting (i) an Si—H containing siloxane with (ii) a compound of the formula Vi-O—$(CH_2)_{0-50}$—CH=$CH_2$ or $CH_2$=CH—$(CH_2)_{0-50}$-Vi-O—$(CH_2)_{0-50}$—CH=$CH_2$ or Vi-O—$(CH_2)_{0-50}$—C≡CH or CH≡C—$(CH_2)_{0-50}$-Vi-O—$(CH_2)_{0-50}$—C≡CH where Vi is a uv-visible absorbing moiety selected from the group consisting of hydroxyanthraquinone having alkenyl or alkynyl functionality;

in the presence of a catalyst and a solvent to obtain the reaction product.

4. A process as claimed in claim 3 wherein the reaction is carried out in the presence of a difunctional spacer compound having alkenyl or alkynyl groups.

5. A process as claimed in claim 3 comprising the step of adding the reaction product to a swelling agent.

6. A process as claimed in claim 4 wherein the difunctional spacer group is of the formula

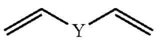

Or

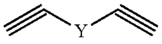

where Y is an organic moiety containing carbon, nitrogen, phosphorous, sulphur, oxygen or silicon atoms.

7. A process as claimed in claim 6 wherein Y is selected from a group consisting of hydrocarbons, polysiloxanes, polyethers, polycarboxylic acids, or polysaccharides.

8. A process as claimed in claim 4 wherein the difunctional spacer compound is selected from the group consisting of di alkenyl polyethers, alpha omega dienes, alpha omega diynes; alpha omega ene-ynes or di alkenyl or dialkynyl terminated polysiloxane.

9. A process as claimed in claim 3 wherein the Si—H containing siloxane is of the general formula:

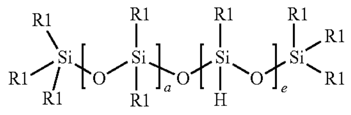

where a and e are integers 1-10,000.

10. A process as claimed in claim 3 wherein step (a) is carried out in the presence of a monofunctional organic moiety of the general formula

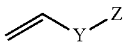

Or

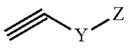

where z is —R1 or —OH or —H;

or

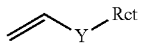

Or

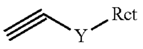

where Rct is a reactive group containing carbon, nitrogen, phosphorous, sulphur, oxygen or silicon atoms.

11. A process as claimed in claim 3 wherein the solvent is selected from the group consisting of water, a silicone fluid, polar organic compound, a non-polar organic compound and a mixture thereof.

12. A process as claimed in claim 5 wherein said swelling agent is a solvent as claimed in claim 11 with the exception of water or alcohol.

13. A process as claimed in claim 12 wherein said swelling agent is a silicone fluid or a functional silicone fluid.

14. A photoprotective personal care composition comprising 0.01 to 10% by weight the silicone compound as claimed in claim 1.

15. A sunscreen agent comprising the silicone compound as claimed in claim 1.

* * * * *